(12) United States Patent
Minai et al.

(10) Patent No.: US 8,018,485 B2
(45) Date of Patent: Sep. 13, 2011

(54) IMAGING DEVICE

(75) Inventors: Tetsuo Minai, Hachioji (JP); Kazuaki Tamura, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/760,853

(22) Filed: Apr. 15, 2010

(65) Prior Publication Data

US 2010/0265321 A1    Oct. 21, 2010

Related U.S. Application Data

(63) Continuation of application No. PCT/JP2009/068019, filed on Oct. 19, 2009.

(30) Foreign Application Priority Data

Oct. 17, 2008   (JP) .................................. 2008-268895

(51) Int. Cl.
    *A61B 1/04*    (2006.01)
    *A61B 1/06*    (2006.01)

(52) U.S. Cl. ........................................................ 348/68

(58) Field of Classification Search ........................ None
    See application file for complete search history.

(56) References Cited

U.S. PATENT DOCUMENTS

| | | | |
|---|---|---|---|
| 4,819,077 A | 4/1989 | Kikuchi et al. | |
| 6,091,445 A | 7/2000 | Matsui et al. | |
| 6,134,030 A | 10/2000 | Kaneko et al. | |
| 7,373,006 B2 * | 5/2008 | Fukuzawa | 382/240 |
| 7,444,031 B2 * | 10/2008 | Fukuzawa | 382/240 |
| 7,728,845 B2 * | 6/2010 | Holub | 345/589 |
| 2004/0225189 A1 | 11/2004 | Kimoto et al. | |
| 2005/0124858 A1 | 6/2005 | Matsuzawa et al. | |
| 2006/0251408 A1 | 11/2006 | Konno et al. | |

FOREIGN PATENT DOCUMENTS

| | | |
|---|---|---|
| JP | 62-266028 | 11/1987 |
| JP | 6-319042 | 11/1994 |
| JP | 9-97363 | 4/1997 |
| JP | 9-138201 | 5/1997 |
| JP | 9-321998 | 12/1997 |

(Continued)

OTHER PUBLICATIONS

Abstract only of Japanese Patent Application Laid-Open Publication No. JP 2005-288191.

(Continued)

*Primary Examiner* — Nhon T Diep
(74) *Attorney, Agent, or Firm* — Scully, Scott, Murphy & Presser, P.C.

(57) ABSTRACT

An imaging device includes first light sources that have first frequency characteristics; second light sources that have second frequency characteristics different from the first frequency characteristics and that are arranged in positions different from those of the first light sources; an imaging unit that generates an image of a subject by receiving light that is emitted from the first light sources and the second light sources and then reflected from an object; and an image corrector that performs color unevenness correction on the image, which is captured by the imaging unit, using correction data with which a ratio of luminance of a first image, which is captured by the imaging unit using the first light sources, with respect to luminance of a second image, which is captured by the imaging unit using the second light sources, in each area is uniform based on the first image and the second image.

1 Claim, 8 Drawing Sheets

FOREIGN PATENT DOCUMENTS

| | | |
|---|---|---|
| JP | 10-75354 | 3/1998 |
| JP | 2002-325729 | 11/2002 |
| JP | 2004-167008 | 6/2004 |
| JP | 2005-80713 | 3/2005 |
| JP | 2005-211231 | 8/2005 |
| JP | 3782093 | 3/2006 |
| JP | 2006-246199 | 9/2006 |
| JP | 2006-524097 | 10/2006 |
| JP | 2007-244590 | 9/2007 |
| JP | 2008-118635 | 5/2008 |
| WO | WO 04/000265 A2 | 12/2003 |
| WO | WO 2004/096029 | 11/2004 |
| WO | WO 2005/071372 A1 | 8/2005 |
| WO | WO 2008/105370 A1 | 9/2008 |

OTHER PUBLICATIONS

Decision on Patent Grant dated Aug. 31, 2010 received from the Japanese Patent Office with English translation.

* cited by examiner

IMAGING DEVICE

CROSS-REFERENCE TO RELATED APPLICATIONS

This application is a continuation of PCT international application Ser. No. PCT/JP2009/068019 filed on Oct. 19, 2009 which designates the United States, incorporated herein by reference.

BACKGROUND OF THE INVENTION

1. Field of the Invention

The present invention relates to an imaging device that captures a multi-spectral image, which is generated from specific color components, and that corrects color variations in the multi-spectral image.

2. Description of the Related Art

In recent years, in the field of endoscopy, capsule body-insertable apparatuses (for example, capsule endoscopes) have been proposed that are provided with an imaging function and a radio communication function and body-insertable apparatus systems have been developed that acquire in-vivo images of a subject by using the capsule endoscope. A capsule endoscope is, for example, swallowed by a patient in order to observe (examine) the interior of the subject. Thereafter, the capsule endoscope moves through the body cavity, such as the internal organs including the stomach and the small intestine, by peristalsis of the internal organs until the capsule endoscope is naturally discharged. While moving, the capsule endoscope functions to capture in-vivo images of the subject at intervals of, for example, 0.5 second.

While the capsule endoscope moves through the inside of the subject, images that are captured by the capsule endoscope are received by an external image display device via antennae that are arranged on the body surface of the subject. The image display device has a function for communicating by radio with the capsule endoscope and an image memory function. The image display device sequentially stores the in-vivo images of the subject, which are received from the capsule endoscope, in a memory. A doctor or a nurse can observe (examine) the interior of the subject and diagnose the subject through display of the in-vivo images of the alimentary canal of the subject.

Japanese Patent No. 3782093 describes a swallowable capsule that captures in-vivo images. The capsule can change the intensity and/or duration in accordance with the amount of illumination that is generated by an in-vivo imaging device and then reflected by the in-vivo imaging device.

SUMMARY OF THE INVENTION

An imaging device according to an aspect of the present invention includes a plurality of first light sources that have first frequency characteristics; a plurality of second light sources that have second frequency characteristics different from the first frequency characteristics and that are arranged in positions different from those of the first light sources; an imaging unit that generates an image of a subject by receiving light that is emitted from the first light sources and the second light sources and then reflected from an object; and an image corrector that performs color unevenness correction on the image, which is captured by the imaging unit, using correction data with which a ratio of luminance of a first image, which is captured by the imaging unit using the first light sources, with respect to luminance of a second image, which is captured by the imaging unit using the second light sources, in each area is uniform on the basis of the first image and the second image.

An imaging device according to another aspect of the present invention includes a plurality of first light source means having first frequency characteristics; a plurality of second light source means having second frequency characteristics different from the first frequency characteristics, the plurality of second light source means being arranged in positions different from those of the first light source means; an imaging means for generating an image of a subject by receiving light that is emitted from the first light source means and the second light source means and then reflected from an object; and an image correcting means for performing color unevenness correction on the image, which is captured by the imaging means, using correction data with which a ratio of luminance of a first image, which is captured by the imaging means using the first light source means, with respect to luminance of a second image, which is captured by the imaging means using the second light source means, in each area is uniform on the basis of the first image and the second image.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Embodiments of an imaging device and an imaging system using the imaging device according to the present invention will be explained in detail below with reference to the drawings. The following embodiments will be explained using capsule endoscope systems as examples. However, the present invention is not limited to those embodiments.

First Embodiment

Figure 1:
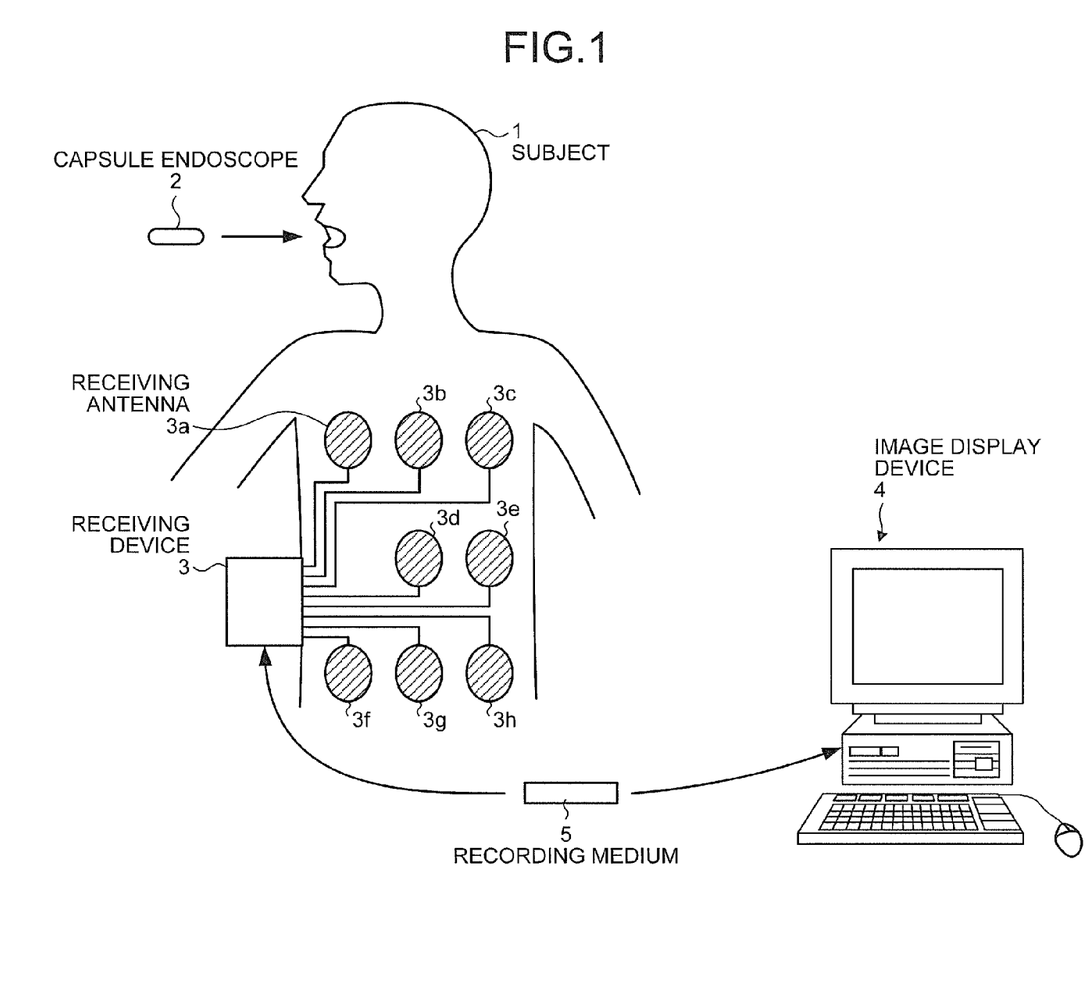
FIG. 1 is a diagram of an entire configuration of a capsule endoscope system that serves as an imaging system according to a first embodiment of the present invention.

FIG. 1 is a schematic diagram of a configuration of a capsule endoscope system according to a first embodiment of the present invention. As illustrated in FIG. 1, the endoscope system according to the first embodiment includes a capsule endoscope 2 that captures in-vivo images of a subject 1; a receiving device 3 that receives image signals that are transmitted by radio from the capsule endoscope 2; an image display device 4 that displays the in-vivo images, which are captured by the capsule endoscope 2; and a portable recording medium 5 for receiving and passing data between the receiving device 3 and the image display device 4.

The capsule endoscope 2 has an imaging function and a radio communication function inside a capsule-shaped casing. The capsule endoscope 2 is introduced, for example, perorally to the internal organs of the subject 1. Thereafter, the capsule endoscope 2 sequentially captures in-vivo images of the subject 1 at predetermined intervals (for example, every 0.5 second) while moving through the internal organs of the subject 1, for example, by peristalsis. Specifically, the capsule endoscope 2 emits blue light and green light from blue and green light emitting devices that are arranged at different positions and captures images of an object illuminated with the illuminating light, i.e., in-vivo images, such as spectral images that are blood-vessel images. The capsule endoscope 2 transmits the image signals of the in-vivo images of the subject 1, which are captured as described above, by radio to the external receiving device 3. The capsule endoscope 2 repeats the operations for sequentially capturing in-vivo images and transmitting in-vivo images by radio from when the capsule endoscope 2 is inserted into the internal organs of the subject 1 until it is discharged to the outside of the subject 1.

The receiving device 3 includes receiving antennae 3a to 3h and receives radio signals from the capsule endoscope 2 in the subject 1 via at least one of the receiving antennae 3a to 3h. The receiving device 3 extracts image signals from the radio signals transmitted from the capsule endoscope 2 and acquires image data of the in-vivo images that are contained in the extracted image signals.

The receiving device 3 includes an image processor that performs image processing on the acquired image data. This processing includes a color unevenness correction process for correcting color unevenness in an image. The receiving device 3 stores a group of processed in-vivo images, on which image processing has been performed, in the recording medium 5. The receiving device 3 associates each image of the in-vivo image group with time data, such as the image capturing time or receiving time.

The receiving antennae 3a to 3h of the receiving device 3 may be arranged on the body surface of the subject 1 as illustrated in FIG. 1 or they may be arranged on a jacket that the subject 1 wears. It is sufficient if the number of receiving antennae of the receiving device 3 is at least one. The number of receiving antennae is not particularly limited to eight.

The image display device 4 is configured like a work station that reads various types of data, such as a group of in-vivo images of the subject 1, via the recording medium 5 and displays the various types of data that have been read, such as the in-vivo image group. Specifically, the recording medium 5, which is detached from the receiving device 3, is attached to the image display device 4, and the image display device 4 acquires the various types of data, such as the group of in-vivo images of the subject 1, by reading the data saved in the recording medium 5. The image display device 4 has a function of displaying the acquired in-vivo images on the display. Diagnosis is performed using the image display on the image display device 4.

The recording medium 5 is another portable recording medium for receiving and passing data between the receiving device 3 and the image display device 4. The recording medium 5 is configured to be attachable to and detachable from the receiving device 3 and the image display device 4 and to output and to record data when it is inserted in the receiving device 3 or the image display device 4.

Specifically, when the recording medium 5 is inserted in the receiving device 3, the recording medium 5 records the group of in-vivo images, on which image processing is performed by the receiving device 3, and time data for each image.

Figure 2:
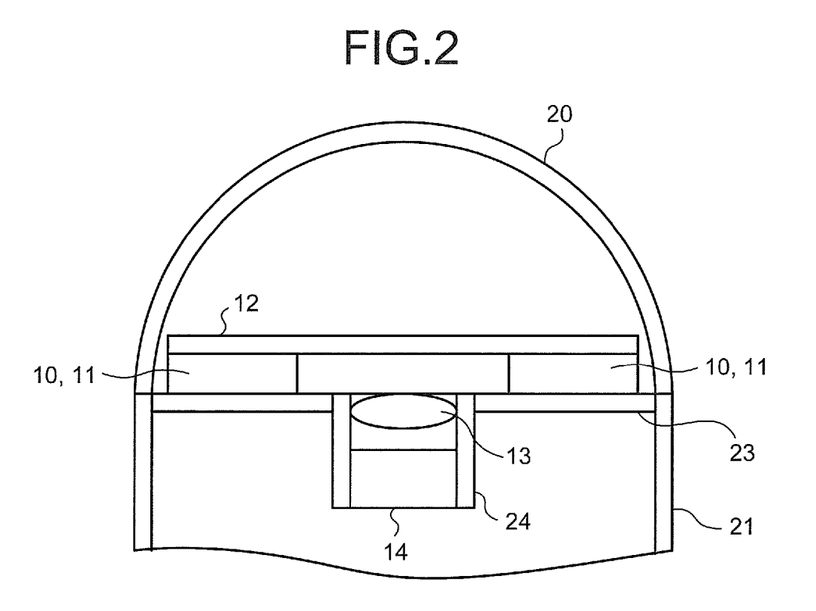
FIG. 2 is a plane view of an imaging unit, an illuminating unit, and the vicinity thereof according to the first embodiment of the present invention.
Figure 3:
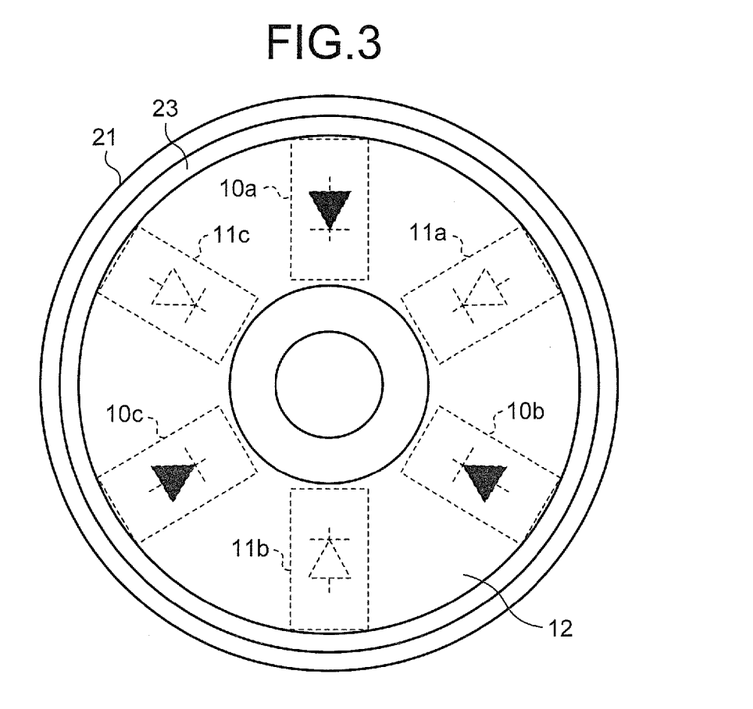
FIG. 3 is a cross-sectional view of the imaging unit, the illuminating unit, and the vicinity thereof according to the first embodiment of the present invention.

The capsule endoscope 2 has various functions in a capsule-shaped casing 21. One end of the capsule-shaped casing 21 is covered with a dome-shaped transparent cover 20. On the other end, the illuminating unit and the imaging unit are arranged. As illustrated in FIGS. 2 and 3, a lens barrel 24 is provided at the center of a circular platy board 23. In the lens barrel 24, an optical lens 13, the optical axis of which is the barrel axis of the capsule-shaped casing 21, and an imaging element 14 are provided. On the peripheral side of the board 23, there are three LEDs 10a to 10c (10) that serve as light emitting devices with a wavelength spectrum having a peak around 415 nm (blue) (the curve Lb represented in FIG. 5) and three LEDs 11a to 11c (11) that serve as light emitting devices with a wavelength spectrum having a peak around 540 nm (green) (the curve Lg represented in FIG. 5). These LEDs are arranged annularly in different positions alternately. A transparent fixing member 12 is provided on the LEDs 10 and 11. A fluorescent member may be provided on the LED 10 such that the fluorescent member is excited by 415-nm light, which is emitted from the LED 10, and thus 540-nm fluorescence is emitted.

Figure 4:
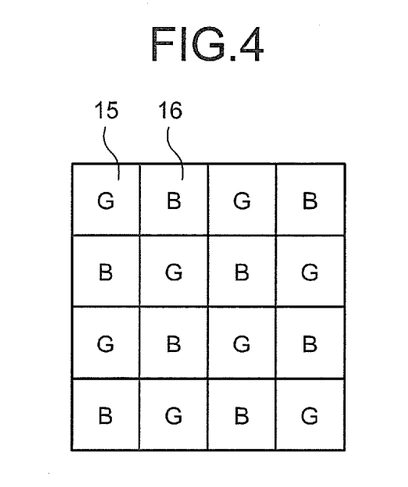
FIG. 4 is a diagram of an example of a pixel array of an imaging element with which the capsule endoscope is provided according to the first embodiment of the present invention.

As illustrated in FIG. 4, the pixels of the imaging element are only green (G) pixels 15 and blue (B) pixels 16, as illustrated in FIG. 2. A commonly used imaging element, such as a Bayer array, may be used. However, red (R) pixels will not be used.

Figure 5:
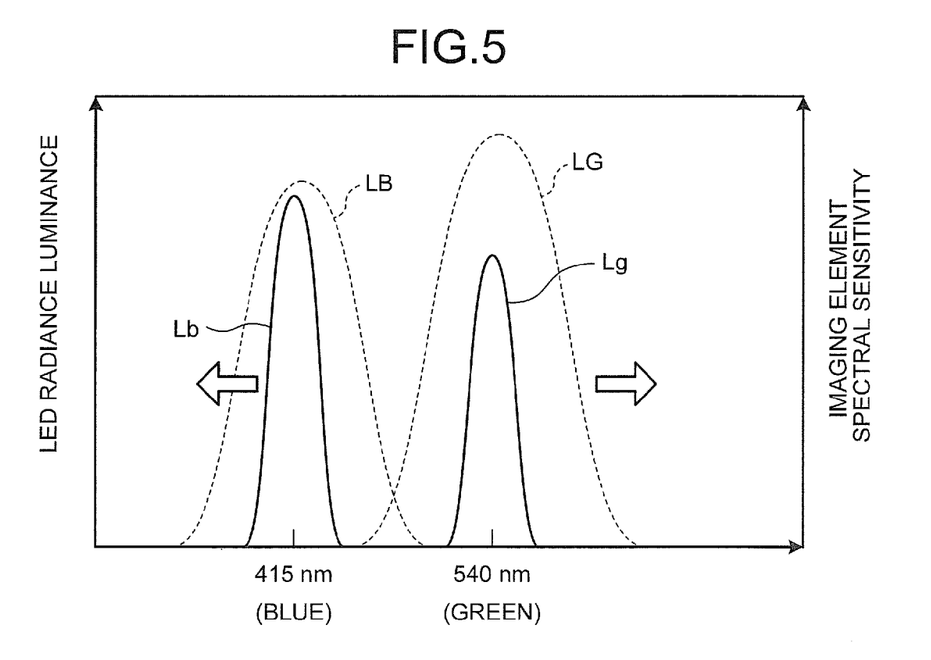
FIG. 5 is a graph representing radiance of a light emitting device and spectral sensitivity of the imaging element according to the first embodiment of the present invention.

A spectral image obtained using 415-nm light (blue) and 540-nm light (green) will be explained below. As illustrated in FIG. 5, the LEDs 10 and 11 have the LED radiance indicated by the curves Lb and Lg, which is emission spectra, and the pixels 15 and 16 have imaging-device spectral sensitivity indicated by the curves LB and LG, which is light receiving spectra.

Figure 6:
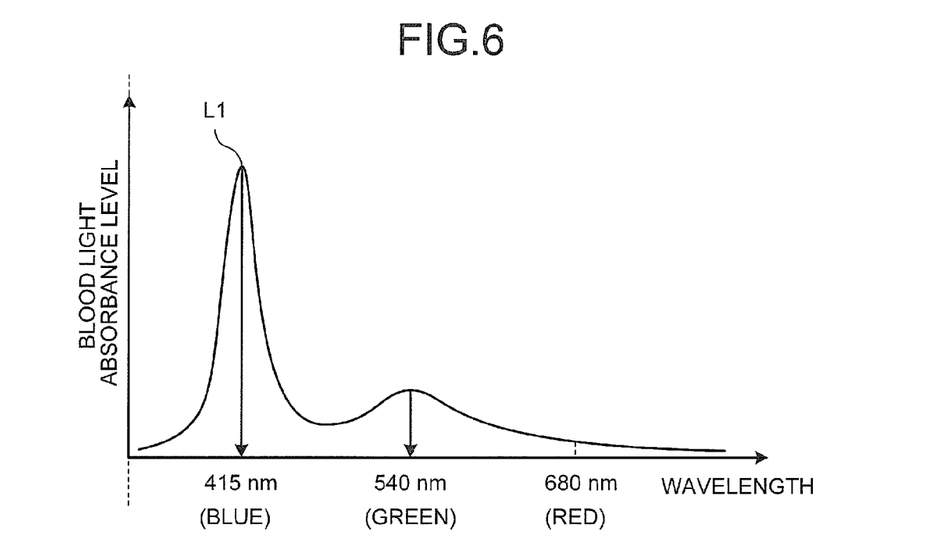
FIG. 6 is a graph representing wavelength dependence in accordance with the blood light absorbance level.
Figure 7:
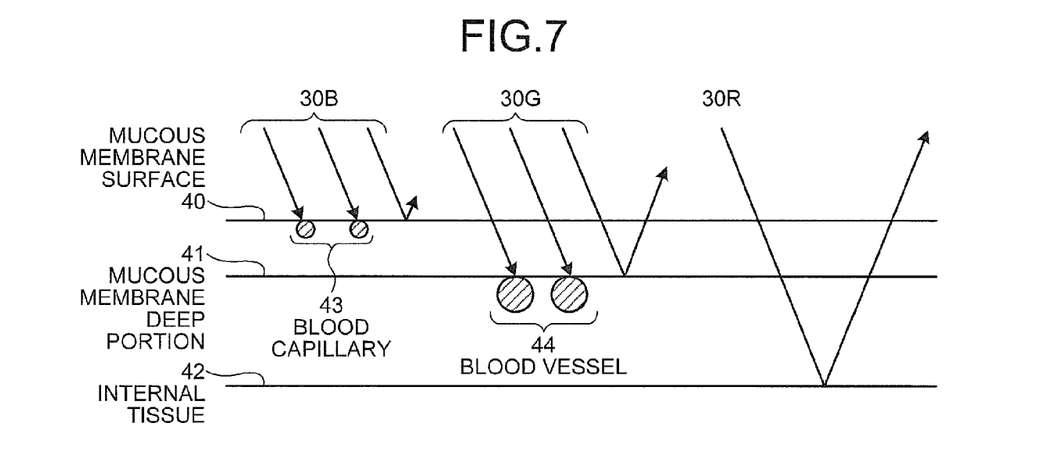
FIG. 7 is a schematic diagram representing the relation between incidence and reflection of light with respect to the interior of the body cavity and the blood vessels.

The blood light absorbance level is low except for the peaks at 415 nm (blue) and 540 nm (green), as illustrated in FIG. 6. Furthermore, as illustrated in FIG. 7, there are blood capillaries 43 on a mucous membrane surface 40 in the inner wall in the body cavity, and there are thick blood vessels 44 in a mucous membrane deep portion 41. The 415-nm light (blue) that is applied to the inner wall in the body cavity is not transmitted to the tissue inner portion because of its short wavelength and it is absorbed by the blood capillaries 43 because of the above-described blood light absorbance. The 540-nm light (green) is transmitted to the mucous membrane deep portion 41 because its wavelength is longer than that of the blue light and it is absorbed by the thick blood vessels 44 because of the above-described blood light absorbance. Red light is transmitted to an internal tissue 42 and is mostly reflected as scattered light. For this reason, if the sensitivity to receiving light is only of 415 nm (blue) and 540 nm (green), contrast information for a blood vessel image of the blood capillaries 43 and the thick blood vessels 44 can be obtained.

Thus, by applying light in blue and green wavelengths to an object and using an imaging element that has sensitivity to these blue and green wavelengths, blood contrast information is obtained and a spectral image, which is a blood vessel image, can be obtained.

When a synthesized image is generated by synthesizing an image of blue light that is mainly received by the pixels 15 of the imaging element 14 and an image of green light that is mainly received by the pixels 16, color unevenness occurs in the image because the LEDs 10 and 11 of the respective colors are arranged in different positions. As described above, this color unevenness in spectral images is corrected by the receiving device 3.

Figure 8:
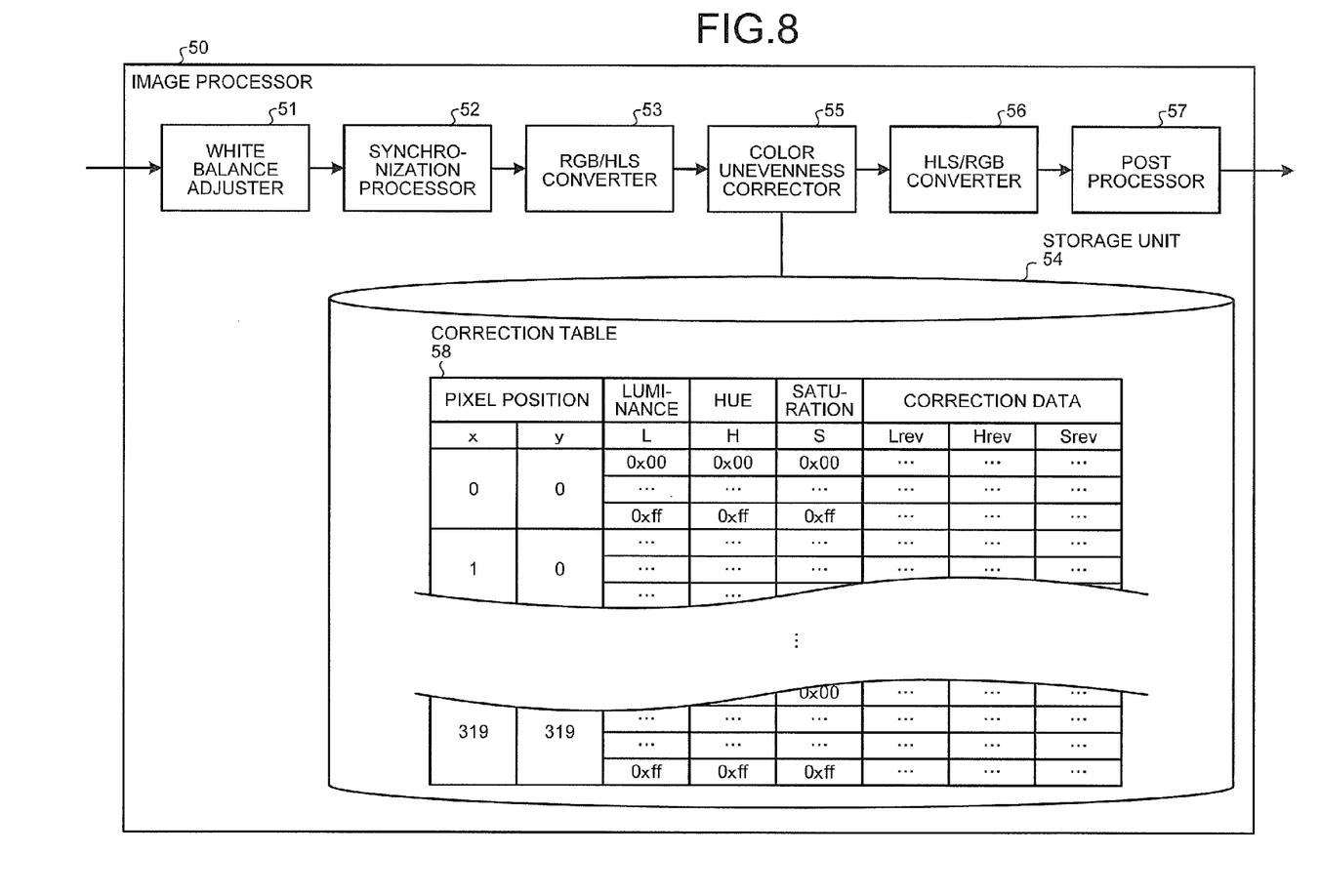
FIG. 8 is a block diagram of a detailed configuration of an image processor with which a receiving device is provided according to the first embodiment of the present invention.

FIG. 8 is a block diagram of a detailed configuration of an image processor 50 that is incorporated in the receiving device 3. As illustrated in FIG. 8, the image processor 50 includes a white balance adjuster 51 that performs white balance adjustment on the image data, which is obtained by converting radio signals transmitted by radio to baseband signals; a synchronization processor 52 that performs color balance correction between pixels on the image data, on which white balance adjustment has been performed; an RGB/HLS converter 53 that converts the synchronized image data to HLS data, which is color space data on hue, luminance, and saturation; a storage unit 54 that includes a correction table 58; a color unevenness corrector 55 that performs color unevenness correction on the HLS data by using the correction table 58; an HLS/RGB converter 56 that inversely converts the HLS data, on which the color unevenness correction has been performed, to RGB data; and a post processor 57 that, if necessary, performs post processing, such as a γ process or structure enhancement, on the image data that is RGB data, which is obtained through the inverse conversion, and outputs the data.

The correction table 58 stores correction data (luminance value Lrev, hue value Hrev, and saturation value Srev) in association with each x-y pixel position in acquired one-frame image data. Correction data is used for correcting image data on all combinations of the luminance value L, the hue value H, and the saturation value S. As illustrated in FIG. 8, image data on all combinations of the luminance value L, the hue value H, and the saturation value S with respect to each x-y pixel position, i.e., 256×256×256 pieces of image data, which are combinations of 256 luminance values L, 256 hue values H, and 256 saturation values S, is stored. If there are 320 pixel positions, there are 256×256×256×320 pairs of image data and correction data. The pixel data in each x-y pixel position in the input HLS data is individually corrected.

Figure 9:
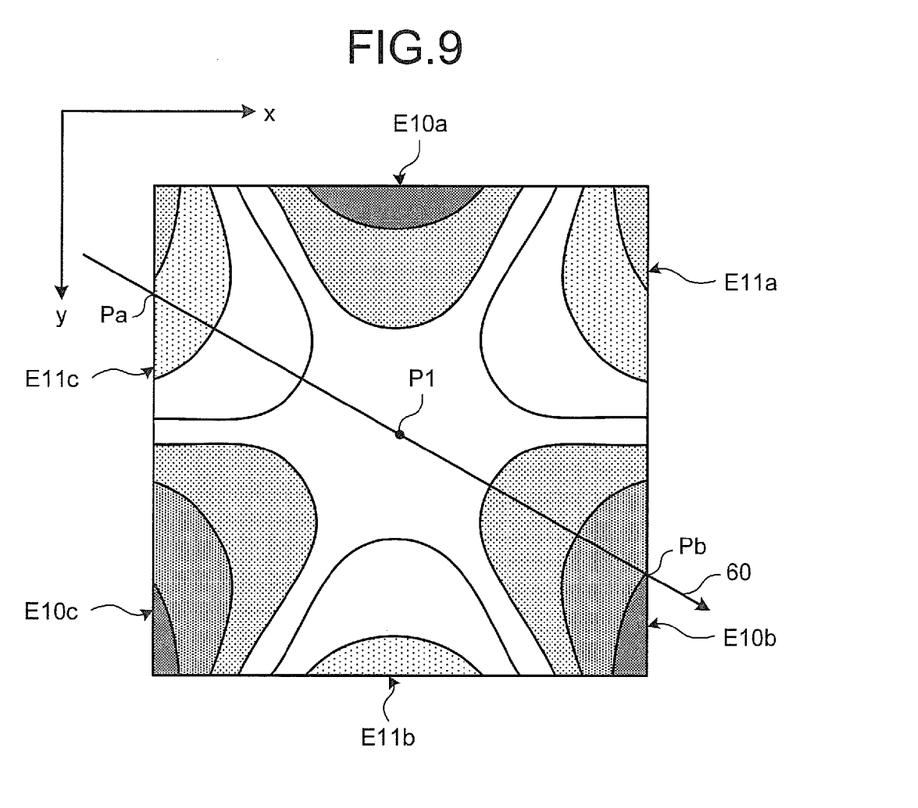
FIG. 9 is a diagram of an example of an image with color unevenness.
Figure 10:
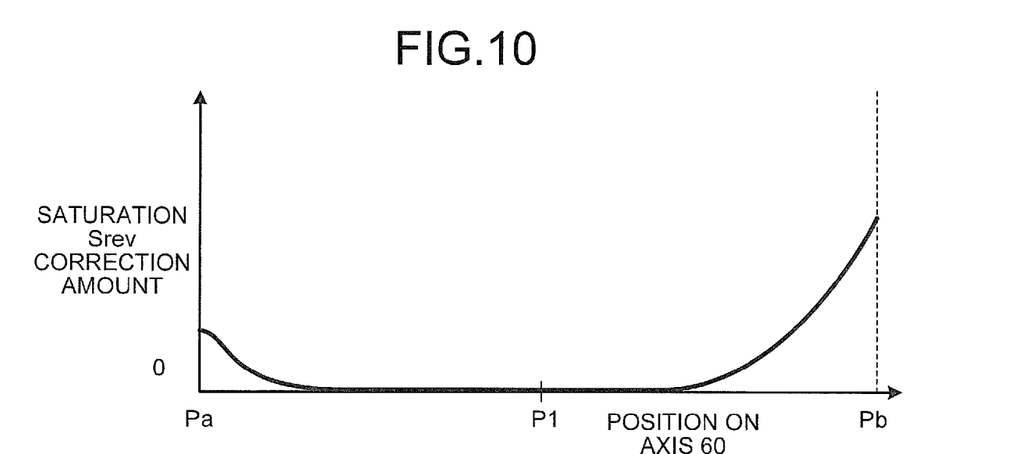
FIG. 10 is a graph representing position dependence that represents the amount of correction for saturation correction data according to the first embodiment of the present invention.

FIG. 9 represents an example of image data on which color unevenness correction has not been performed. As represented in FIG. 9, color unevenness occurs in areas E10a to E10c that correspond respectively to positions where the LEDs 10a to 10c are arranged and color unevenness occurs in areas E11a to E11c corresponding to positions where the LEDs 11a to 11c are arranged. Thus, the correction data in the correction table 58 contains values for individually correcting the color evenness with respect to each x-y pixel position. In addition, each piece of correction data in the correction table 58 is beforehand obtained individually. For example, the amount of correction for the saturation value Srev for pixels on the line axis 60 is as represented in FIG. 10, i.e., saturation around both ends Pa and Pb is corrected greatly. The amount of correction for the saturation value Srev is adjusted according to the luminance value L, the hue value H, and the saturation value S. The value that reflects the correction amount is the saturation value Srev. The luminance value Lrev and the hue value Hrev with the same luminance value L, hue value H, and saturation value S are similarly determined. With the correction data, correction is performed such that the ratio of each luminance value of blue image data with respect to each luminance value of green image data is eventually uniform. In the first embodiment, the RGB color space is converted to the HLS color space, the luminance value of each area is corrected, the luminance of each area is corrected, and the hue and saturation in accordance with the variations in luminance are corrected.

The correction data is obtained beforehand. There is a premise that acquired correction data is used in an environment in which images of the object are almost the same as that represented in FIG. 9. For example, because the LEDs 10 and 11 are arranged annularly, it can be considered that, when correction data is acquired, the object surface for correction is a plane that is perpendicular to the optical axis of the optical lens 13, a plane that is symmetrical to the optical axis, a curved surface that is symmetrical to the optical axis, or a surface that is set on the basis of the space frequency characteristics of the optical lens.

In the first embodiment, the RGB color space is converted to the HLS color space and color unevenness correction is performed on the image data in the HLS color space. Alternatively, color unevenness correction may be performed directly in the RGB space because the HLS color space is eventually converted to the RGB space. In this case, the configuration for the RGB/HLS converter 53 and the HLS/RGB converter is unnecessary. Accordingly, the conversion process time can be eliminated.

In the first embodiment, all color components in the HLS color space, i.e., all of luminance, hue, and saturation, are corrected. Alternatively, at least one component, for example, only hue or only saturation may be corrected. This also leads to the same effects of color unevenness correction.

In the first embodiment, color unevenness in a spectral image, which is obtained using light emitting devices having different wavelength bands and arranged in different positions, is corrected.

In the first embodiment, the receiving device 3 includes the color unevenness corrector 55, the correction table 58, the RGB/HLS converter 53, and the HLS/RGB converter 56. Alternatively, the image display device 4 may include these units.

Second Embodiment

Figure 11:
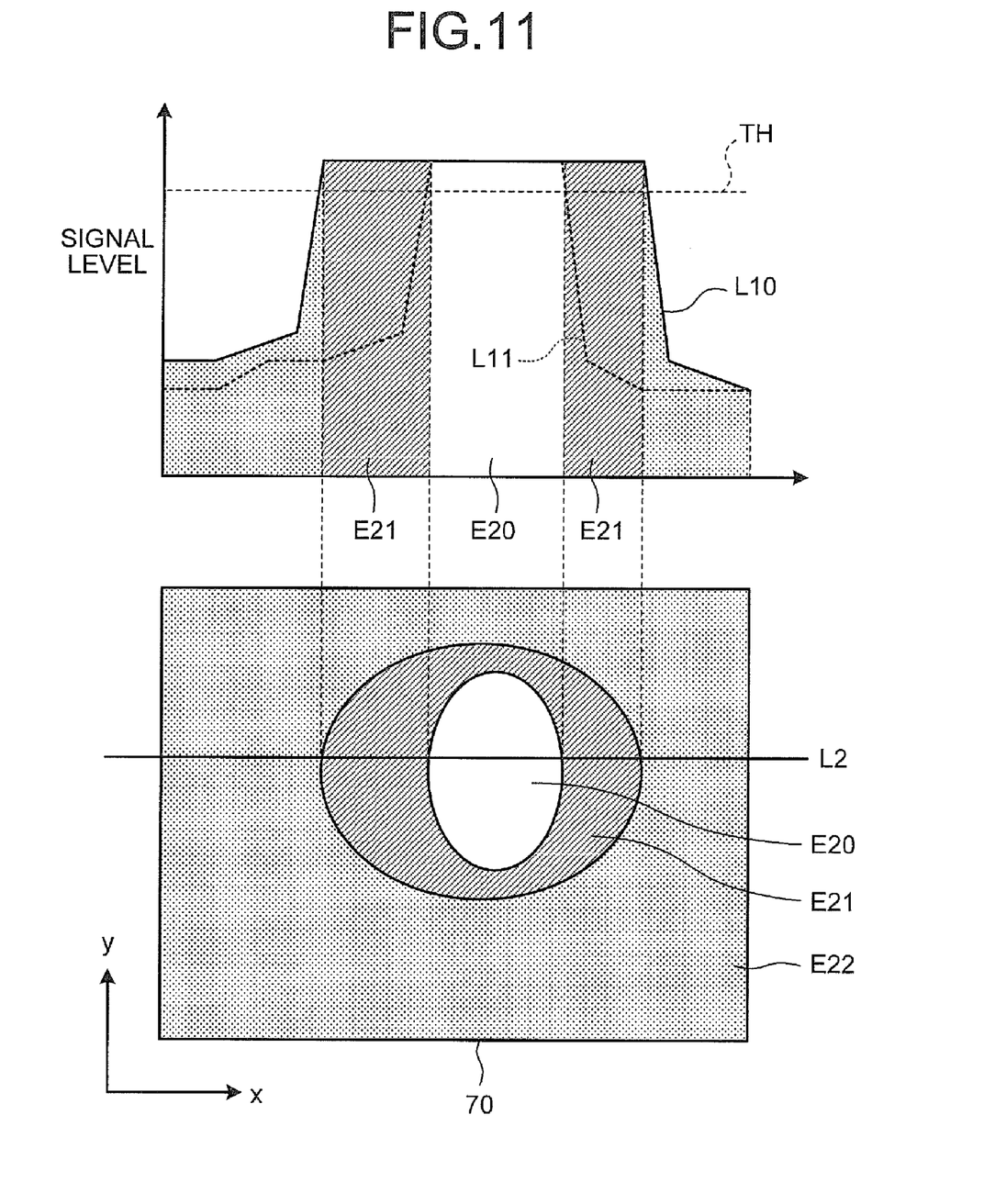
FIG. 11 is a diagram representing an example of a high luminance area and a fake color area according to a second embodiment of the present invention.

A second embodiment of the present invention will be explained below. When illumination light from a light emitting device is reflected specularly, the luminance is saturated in the specular reflection area, which results in a high luminance area. When light emitting devices having blue wavelength band and green wavelength band, which are different from each other, are arranged in different positions, an image is acquired that contains a high luminance area E20 where both of the blue signal level and the green signal level are saturated and a fake color area E21, which is distributed around the high luminance area, where only the blue signal level or the green signal level is saturated. As illustrated in FIG. 11, only the blue signal level is saturated in the fake color area E21.

In the second embodiment, the color unevenness corrector 55 determines whether there is an area where the luminance L exceeds a threshold TH. When there is an area where the threshold TH is exceeded, the color unevenness corrector 55 regards the area as a possible high luminance area. Furthermore, the color unevenness corrector 55 detects on the basis of color information, such as the hue value H around the possible high luminance area, an area where any one of the blue signal and the green signal is not saturated, determines such an area to be the fake color area E21, and determines the remaining possible high luminance area to be the high luminance area E20.

As in the first embodiment, when light emitting devices having different wavelength bands are arranged in different positions, there are a plurality of colors in the fake color area E21. For this reason, to easily distinguish the fake color area E21 from another object image area E22, the color unevenness corrector 55 converts the fake color area E21 with different colors to have uniform color and luminance. Similarly, to distinguish the high luminance area E20 from other subject image areas, the color unevenness corrector 55 converts the high luminance area E20 to have a common color and luminance. In this case, the color unevenness corrector 55 does not perform color unevenness correction using the correction table 58 represented in the first embodiment.

Accordingly, an image is generated in which the high luminance area E20, the fake color area E21, and the other subject image area E22 can be distinguished easily from one another. The color unevenness corrector 55 converts the color and luminance in the high luminance area E20 and the fake color area E21. This includes displaying in black. However, the display is not limited to this. For example, flash displaying in the areas may be performed.

Third Embodiment

A third embodiment according to the present invention will be explained below. In the third embodiment, the occurrence of color unevenness is inhibited beforehand as much as possible by changing the luminous intensity distribution of the light emitting devices having the blue wavelength band and the green wavelength band, which are arranged in different positions, i.e., changing the light emission directivity.

Figure 12:
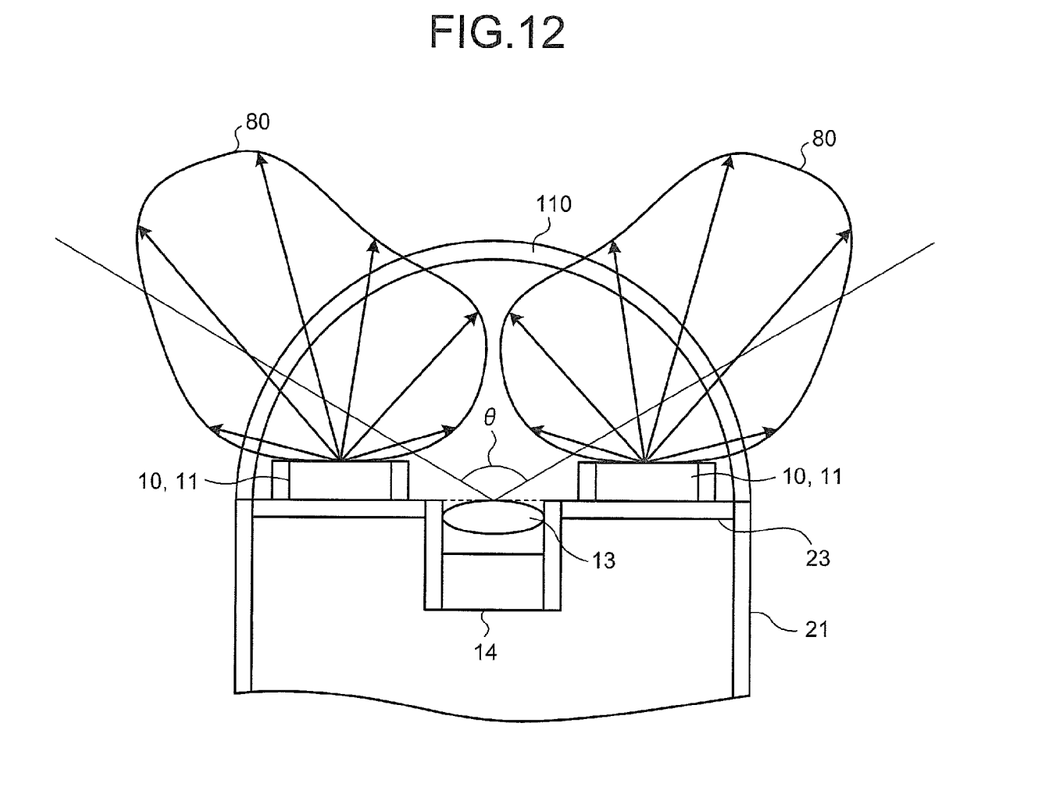
FIG. 12 is a diagram representing an example of luminous intensity distribution that reduces color unevenness resulting from the arrangement of LEDs according to a third embodiment of the present invention.

When the LEDs 10 and 11 are arranged annularly as illustrated in FIG. 3, an image with color unevenness is obtained as illustrated in FIG. 9. Color unevenness occurs in the outer areas in this image because the LEDs emit light omnidirectionally and thus the light emission level in the radially outward direction is low. For this reason, by arranging the LEDs such that the light emission directivity 80 results in an increase in radially outward light emission, as illustrated in FIG. 12, the luminance distribution of an acquired image becomes even, which makes beforehand the color unevenness small. It is preferable that the circumferential light emission directivity be uniform. To cancel out the circumferential color unevenness distribution, it is required to circumferentially arrange the LEDs densely. In this case, because an LED has an anode on one of its longitudinal one ends and a cathode on the other end and the anode has greater light emission directivity, the above-described luminous intensity distribution can be obtained only by arranging the LEDs such that anode are facing radially outward.

In the third embodiment, light emitting devices are arranged such that their luminous intensity distribution is varied to reduce color unevenness in images to be acquired. This reduces beforehand color unevenness in an image on which color correction is to be performed. Particularly when LEDs are used as light emitting devices, color unevenness can be reduced easily.

According to the above-described embodiments, an image corrector performs color unevenness correction on an image, which is captured by an imaging unit, using correction data with which a ratio of luminance of a first image, which is captured by the imaging unit using first light sources, with respect to luminance of a second image, which is captured by the imaging unit using second light sources, in each area is uniform on the basis of the first image and the second image. Thus, even if first and second light sources, which are different from each other and emit light in different wavelength bands, are arranged in different positions and spectral images are obtained, color unevenness can be removed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device comprising:
    a plurality of first light sources that have first frequency characteristics;
    a plurality of second light sources that have second frequency characteristics different from the first frequency characteristics and that are arranged in positions different from those of the first light sources;
    an imaging unit that generates an image of a subject by receiving light that is emitted from the first light sources and the second light sources and then reflected from an object; and
    an image corrector that performs color unevenness correction on the image, which is captured by the imaging unit, using correction data with which a ratio of luminance of a first image, which is captured by the imaging unit using the first light sources, with respect to luminance of a second image, which is captured by the imaging unit using the second light sources, in each area is uniform on the basis of the first image and the second image,
    wherein the image corrector detects a high luminance area, in which a luminance value is a predetermined value or larger, in each area in the first image and the second image and a fake color area, in which a luminance value of any one of the first image and the second image is the predetermined value or larger and a luminance value of the other image is smaller than the predetermined value, in each area in the first image and the second image,
    the image corrector changes, when detecting the high luminance area, the high luminance area to color component data or display modes that represent the high luminance area, instead of the color unevenness correction, and
    the image corrector changes, when detecting the fake color luminance area, the fake color luminance area to color component data or display modes that represent the fake color area, instead of the color unevenness correction.

* * * * *